(12) United States Patent
Fercher

(10) Patent No.: US 7,656,537 B2
(45) Date of Patent: Feb. 2, 2010

(54) DEVICE FOR DETERMINING THE POSITION OF SPACED-APART AREAS IN TRANSPARENT AND/OR DIFFUSE OBJECTS

(75) Inventor: Adolf Friedrich Fercher, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 11/792,279

(22) PCT Filed: Jan. 28, 2006

(86) PCT No.: PCT/EP2006/000751

§ 371 (c)(1),
(2), (4) Date: Jun. 4, 2007

(87) PCT Pub. No.: WO2006/081998

PCT Pub. Date: Aug. 10, 2006

(65) Prior Publication Data

US 2007/0291276 A1 Dec. 20, 2007

(30) Foreign Application Priority Data

Feb. 4, 2005 (DE) ...................... 10 2005 005 816

(51) Int. Cl.
*G01B 11/02* (2006.01)
(52) U.S. Cl. ....................... 356/496; 356/497
(58) Field of Classification Search ................. 356/500, 356/497, 479, 496, 452
See application file for complete search history.

(56) References Cited

U.S. PATENT DOCUMENTS

| | | | |
|---|---|---|---|
| 5,825,493 A * | 10/1998 | McGlynn ..................... 356/452 |
| 5,975,697 A * | 11/1999 | Podoleanu et al. .......... 351/206 |
| 6,064,481 A | 5/2000 | Matsumoto et al. |
| 6,385,358 B1 * | 5/2002 | Everett et al. ................. 385/12 |
| 7,177,030 B2 * | 2/2007 | Leizerson et al. ........... 356/504 |
| 2002/0183625 A1 | 12/2002 | Ostrivsky |
| 2005/0140981 A1 * | 6/2005 | Waelti ........................ 356/479 |

FOREIGN PATENT DOCUMENTS

| | | |
|---|---|---|
| DE | 32 01 801 | 4/1992 |
| EP | 1 311 801 | 9/2005 |
| WO | 96/35100 | 11/1996 |
| WO | 01/38820 | 5/2001 |
| WO | 03/086180 | 10/2003 |
| WO | WO 03/086180 * | 10/2003 .................... 653/2 |

* cited by examiner

*Primary Examiner*—Tarifur Chowdhury
*Assistant Examiner*—Michael LaPage
(74) *Attorney, Agent, or Firm*—Reed Smith LLP

(57) ABSTRACT

The invention is directed to a device for determining the thickness, distance and/or profile of areas of a transparent and/or diffuse object that are spaced apart, in particular for measuring distances in the eye. In the device for determining position using an interferometer arrangement based on the Michelson principle, a scanning unit is arranged for the change in path length in the reference beam or measurement beam path. The scanning unit comprises a scan table which is movable translationally in corresponding guides, the movement direction enclosing an angle α to the reference beam. At least two reference mirrors having a distance d in direction of the reference beam and slightly overlapping laterally are arranged on the scan table so that during the oscillating movement of the scan table carried out by a motor the reference beam is reflected in itself first by the first reference mirror and then by the second reference mirror.

9 Claims, 1 Drawing Sheet

DEVICE FOR DETERMINING THE POSITION OF SPACED-APART AREAS IN TRANSPARENT AND/OR DIFFUSE OBJECTS

CROSS-REFERENCE TO RELATED APPLICATIONS

This application claims priority of International Application No. PCT/EP2006/000751, filed Jan. 28, 2006 and German Application No. 10 2005 005 816.7, filed Feb. 4, 2005, the complete disclosures of which are hereby incorporated by reference.

BACKGROUND OF THE INVENTION a) Field of the Invention

The present invention is directed to a method and an arrangement for determining the thickness, distance and/or profile of areas of a transparent and/or diffuse object that are spaced apart. In particular, the solution is suitable for measuring partial distances, i.e., distances between surfaces, interfaces or defects in the eye. The measurement of these partial distances is especially important for cataract surgery and refractive eye surgery.

b) Description of the Related Art

The length of the individual axial eye portions can be determined by means of acoustical or optical length measurement methods. Short-coherence interferometry has been applied to an increasing extent for this purpose owing to the advantages of its contactless, highly precise manner of operation.

For short-coherence interferometry, arrangements based on the Michelson principle are generally used, wherein the beam of a short-coherent radiation source is split into a measurement beam and a reference beam. When the coherence length of the utilized light is less that the optical path length between the interfaces to be measured, no interference occurs between the light bundles reflected by the interfaces. When the measurement beam and reference beam are recombined, the change in path length effected in the reference beam path by means of a reference mirror leads to interference in case the path lengths of the measurement beam and reference beam are identical. The change in path length can be effected, for example, by a translational movement of the reference mirror (DE 32 01 801 C2) or by rotation of a transparent cube (WO 96/35100). The occurring interference patterns are directed to a detector and evaluated in a corresponding manner. The change in path length of the reference beam is a direct measure of the queried distance between the interfaces of the eye.

In classic short-coherence interferometry, the reference mirror travels a path length corresponding to the distance to be measured, while the measured object is at rest. Since it is difficult to fixate an eye for the period of time required to measure distances of approximately 30 mm, special solutions were developed for ophthalmologic applications which also enable measurements of living objects. Measurement errors caused by inadequate fixation of the eye to be measured can be avoided through scanning lengths of only a few millimeters.

In the dual beam method, as it is called, areas of an eye that are spaced apart with respect to depth are illuminated/scanned by two measurement beams simultaneously. The solution described in DE 32 01 801 C2 uses measurement beams of different wavelength which are focused on the cornea and, for example, on the fundus by means of a diffractive optical element. The interferometer arrangement is adjusted to the distance to be measured, for example, between the cornea and fundus, so that a scanning length of only a few millimeters is required.

WO 01/38820 A1 describes a solution in which two areas of an eye which are spaced apart with respect to depth are illuminated/scanned by means of a dual beam. A partial beam is cut out of the measurement beam focused on a first interface in front of the measured object, directed by a so-called diverting unit, and focused on a second interface of the eye. Accordingly, a single measurement encompasses reflections at a plurality of interfaces of the eye almost simultaneously. The beams have different optical characteristics such as, e.g., wavelength, polarization state, or the like, so that the individual reflections can be distinguished from one another. The evaluation of the two measurement beams is carried out through path length change in the reference beam; different interference patterns are also generated for the different measurement beams.

However, the described arrangements have the disadvantage that the measurement beams illuminate/scan two or more interfaces simultaneously so that the radiation not contributing to the measurement generates background interference and noise. The less precise the adjustment of the interferometer arrangement to the distance to be measured, the greater its required scanning area.

OBJECT AND SUMMARY OF THE INVENTION

It is the primary object of the present invention to develop a short-coherent interferometer arrangement by which partial distances in an eye can be measured simply and quickly with high accuracy.

According to the invention, this object is met by a device for determining the position of the spaced-apart areas in transparent and/or diffuse objects using an interferometer arrangement based on the Michelson principle, comprising a scanning unit which is arranged for the change in path length in the reference beam or measurement beam path. The scanning unit comprises a scan table which is movable translationally in corresponding guides, wherein the movement direction encloses an angle α to the reference beam. At least two reference mirrors are included having a distance d in direction of the reference beam and slightly overlapping laterally and which are arranged on the scan table so that during the oscillating movement of the scan table, carried out by a motor, the reference beam is reflected in itself first by the first reference mirror and then by the second reference mirror.

The device according to the invention for determining the position of spaced apart areas in transparent and/or diffuse objects provides for the use of an interferometer arrangement based on the Michelson principle for this purpose. A scanning unit comprising a scan table which is movable in a translational manner in corresponding guides is provided for the path length change in the reference beam path. The movement direction encloses an angle α to the reference beam. At least two reference mirrors having a distance d in direction of the reference beam and slightly overlapping laterally are arranged on the scan table so that during the oscillating movement of the scan table which is carried out by a motor the reference beam is reflected in itself initially by the first reference mirror and then by the second reference mirror.

The device according to the invention is suitable for determining the positions of spaced apart object areas in transparent and/or diffuse objects and particularly for measuring partial distances between surfaces, interfaces or defects in the eye. The measurement of partial distances in the eye is particularly important for cataract surgery and refractive eye surgery and is applied to an increasing extent.

The invention will be described more fully in the following with reference to an embodiment example.

DESCRIPTION OF THE PREFERRED EMBODIMENTS

The device according to the invention for determining the position of spaced apart areas in transparent and/or diffuse objects uses an interferometer arrangement based on the Michelson principle.

A scanning unit is arranged in the reference beam path or measurement beam path for path length change. The scanning unit comprises a scan table which is movable in a translational manner in corresponding guides. The movement direction encloses an angle $\alpha$ to the reference beam.

At least two reference mirrors having a distance d in direction of the reference beam and slightly overlapping laterally are arranged on the scan table so that during the oscillating movement of the scan table which is carried out by a motor the reference beam is reflected in itself initially by the first reference mirror and then by the second reference mirror.

Figure 1:
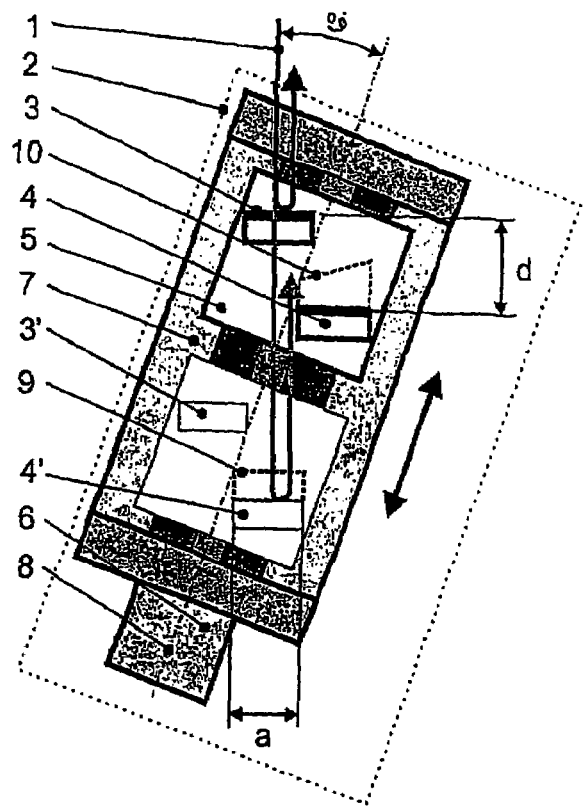
FIG. 1 shows a scanning unit with two reference mirrors.

FIG. 1 shows a first constructional variant of a scanning unit 2 which is to be arranged in the reference beam path 1 and which has two reference mirrors 3 and 4.

The scan table 5 of the scanning unit 2 is moved translationally in an oscillating motion in corresponding guides 7 by a motor 6. The movement direction 8 encloses an angle $\alpha$ to the reference beam 1.

The motor 6 is preferably a stepper motor or piezo motor. But it is also possible to use a voice coil scan table or ultrasonic piezo scan table.

The angle $\alpha$ determines the division of the scan travel into x and y components. At an angle $\alpha$ of 45°, the ratio is 1:1. The components angle $\alpha$, distance d and extension a must be adapted to one another in such a way that the above-stated object can be met by means of the arrangement.

Two reference mirrors 3 and 4 are arranged on the scan table 5 and have in direction of the reference beam 1 a distance d and a lateral extension a which is preferably identical for both reference mirrors 3 and 4.

A slight lateral overlapping of the reference mirrors 3 and 4 ensures that the reference beam 1 is reflected in itself successively by the reference mirrors 3 and 4 during the oscillating movement of the scan table 5 carried out by motor. The reference beam 1 is shown as a deflected beam only for the sake of better comprehension. The oscillating movement of the scan table 5 is illustrated by the scan table 5' with reference mirrors 3' and 4' which is shown in thinner lines. The reference beam 1 is reflected in itself either by reference mirror 3 or 4'.

In an advantageous manner, the distance d of the reference mirrors 3 and 4 can be varied. The scanning period can be substantially reduced by prior adjustment of d to the distance of the spaced apart areas to be determined. The more precisely the adjusted distance d corresponds to the actual value, the shorter the scanning period. The two reference beams accordingly always have a difference in length of 2d.

Further, the scanning unit 2 is advantageously constructed so as to be displaceable in its entirety in order to use the device for different distances to the object to be measured.

The accuracy of the interferometer arrangement is impaired by dispersion in the individual measurement arms. In order to achieve maximum accuracy, the dispersion must be of an identical magnitude in both interferometer arms as far as possible. While the component-related dispersion can be corrected by plane plates of corresponding thickness, two wedge plates which are displaced relative to one another in a corresponding manner are required in the reference beam path to compensate for the object-related dispersion.

Plane plates 9 and/or wedge plates 10 can be arranged in front of the reference mirrors 3 and 4 to compensate for dispersion. Refraction of rays must be taken into account when orientating the reference mirrors 3 and 4.

In another construction, more than two reference mirrors with different distances d can be arranged on the scan table 5. This ensures that the position of more than two spaced apart areas can be determined by one scanning process.

In order to reduce the time required for determining position as much as possible, the scan area should not be substantially greater than the sum of the lateral extension of all of the reference mirrors divided by the sine of angle $\alpha$.

Figure 2:
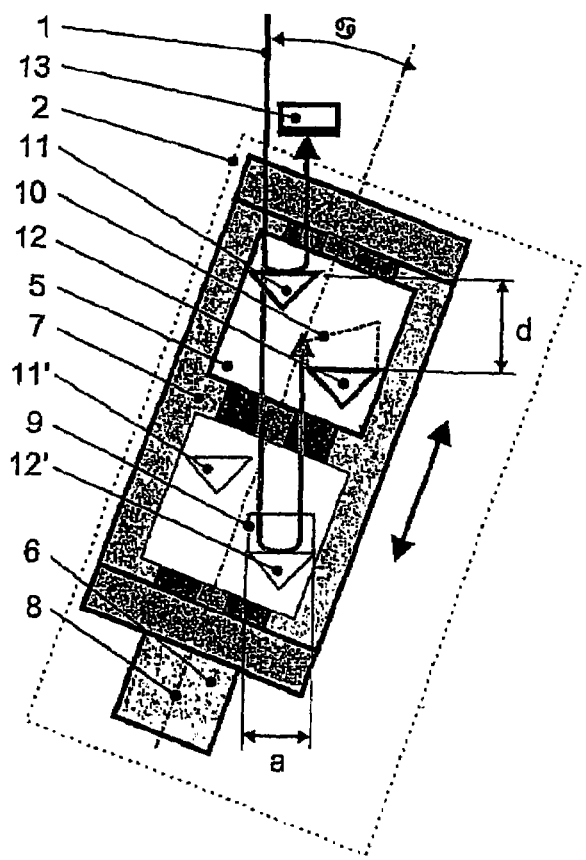
FIG. 2 shows a scanning unit with two prisms serving as reference mirrors.

FIG. 2 shows another advantageous construction in which two prisms 11 and 12 are arranged as reference mirrors on the scan table 5 of the scanning unit 2.

The prisms 11 and 12 can be dimensioned in such a way that wedge plates 10 can be dispensed with. The prism 12 has a longer path in glass to compensate for dispersion.

The scan table 5 is moved translationally in an oscillating motion in corresponding guides 7 by a motor 6. The movement direction 8 encloses an angle $\alpha$ to the reference beam 1.

Two prisms 11 and 12 are arranged on the scan table 5 and have in direction of the reference beam a distance d and a lateral extension a that is preferably identical for both prisms 11 and 12.

A slight lateral overlapping of the prisms 11 and 12 ensures that during the oscillating movement of the scan table 5 by means of the motor the reference beam 1 is deflected on an additionally provided mirror 13 by the two prisms 11 and 12 successively and, after being reflected at this mirror 13, is reflected in itself by another deflection.

Here also, plane plates 9 and/or wedge plates 10 can be arranged in front of the prisms 11 and 12 to compensate for dispersion. Refraction of rays must be taken into account when orientating the reference mirrors 3 and 4.

The reference beam 1 is shown as a deflected beam only for the sake of better comprehension. The oscillating movement of the scan table 5 is illustrated by the scan table 5' with reference mirrors 3' and 4' which is shown in thinner lines. The reference beam 1 is reflected in itself either by prism 11 or prism 12'.

The scan area of the device can be doubled through the use of prisms 11 and 12. The additionally provided mirror 13 can also be constructed as a prism. In this variant, the influence of tilting which is caused by inaccurate arrangement or incorrect guides 7 and which worsens the interferometer signal can be reduced in an advantageous manner.

But it is also possible to arrange a plurality of additional mirrors 13 so that the reference beam 1 which is first deflected by the first prism 11 and then by the second prism 12 is reflected in itself by repeated reflection and by another deflection. The beam path can be advantageously folded by these additional mirrors so that the movement area is increased while the scan travel remains the same.

The reference beams generated in this way are superimposed with the measurement beams reflected at the object areas (interfaces) to be determined, imaged on a detector and evaluated. The change in path length carried out in the reference beam path by means of the reference mirrors 3 and 4 or prisms 11 and 12 leads to interference in case the path lengths of the measurement beam and reference beam are identical. The change in path length of the reference beam is a direct measure of the distance to be determined between the spaced apart areas of the object.

In a variant which is not shown in the drawings, combinations of a reference mirror with a prism are also possible. When, for example, a reference mirror is used as a first deflecting element and a prism is used as a second deflecting element, dispersion can be compensated in a simple manner in that the prism has the corresponding path in glass.

By means of the proposed device, it is possible to scan two or more spaced apart areas of a transparent and/or diffuse object directly one after the other and to determine their position in a measurement process.

In contrast to the prior art solutions, the proposed device requires only one detector at the output of the interferometer because one and the same measurement beam determines the position of the spaced part areas one after the other. Neither different wavelengths nor different polarization states of the measurement beam are required so that the construction of the device is substantially simplified.

By reducing the scan distance to a few millimeters, the position of spaced apart areas can be determined very quickly.

In the proposed device, it is particularly advantageous that the measurement beams are focused on the corresponding areas one after the other because this substantially reduces the scatter light component and improves the signal quality.

While the foregoing description and drawings represent the present invention, it will be obvious to those skilled in the art that various changes may be made therein without departing from the true spirit and scope of the present invention.

What is claimed is:

1. A device for determining the position of spaced apart areas in transparent and/or diffuse objects using an interferometer arrangement based on the Michelson principle, comprising:

a scanning unit being arranged for a change in path length, the scanning unit capable of being arranged in a reference beam path and in a measurement beam path;

said scanning unit comprising a scan table which is movable translationally in corresponding guides, wherein the movement direction encloses an angle $\alpha$ to the reference beam, wherein the angle $\alpha$ does not equal zero; and at least two reference mirrors having a distance d in direction of the reference beam and slightly overlapping laterally, the at least two reference mirrors being arranged on the scan table so that during the oscillating movement of the scan table carried out by a motor the reference beam is reflected in itself first by the first reference mirror and then by the second reference mirror.

2. The device for determining position according to claim 1;

wherein the scanning unit which is arranged in the reference beam path is displaceable in its entirety for adapting to the distance of the object to be measured.

3. The device for determining position according to claim 1;

wherein the distance d of the reference mirrors can be varied to adapt to the distance of the spaced apart areas to be determined.

4. The device for determining position according to claim 1;

wherein more than two reference mirrors can be arranged in a corresponding manner on the scan table so that the position of more than two spaced apart areas can be determined by one scanning process.

5. The device for determining position according to claim 1;

wherein plane plates and/or wedge plates are arranged in front of the reference mirrors to compensate for dispersion, wherein a possible refraction of rays must be taken into account in the orientation of the reference mirrors.

6. The device for determining position according to claim 1;

wherein the scan area is not substantially greater than the sum of the lateral extension a of all of the reference mirrors divided by the sine of angle $\alpha$.

7. The device for determining position according to claim 1;

wherein at least two prisms having a distance d in direction of the reference beam and slightly overlapping laterally are arranged as reference mirrors on the scan table so that during the oscillating movement of the scan table which is carried out by a motor the reference beam is deflected on an additionally provided mirror first by the first prism and then by the second prism and, after being reflected at the additionally provided mirror, is reflected in itself by another deflection.

8. The device for determining position according to claim 7;

wherein a plurality of additional mirrors are provided so that the reference beam which is deflected first by the first prism and then by the second prism is reflected in itself by repeated reflection and by another deflection.

9. The device for determining position according to claim 1;

wherein prisms and reference mirrors can be arranged on the scan table.

* * * * *